(12) United States Patent
Krebs et al.

(10) Patent No.: US 9,408,720 B2
(45) Date of Patent: Aug. 9, 2016

(54) ORTHOPEDIC IMPLANT INSERTER WITH REMOVABLE JAWS

(75) Inventors: Robert D. Krebs, Warsaw, IN (US); Jody L. Claypool, Columbia City, IN (US); John Dockstader, Cedar Park, TX (US); Jeff Blaylock, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 44 days.

(21) Appl. No.: 12/916,127

(22) Filed: Oct. 29, 2010

(65) Prior Publication Data
US 2012/0109225 A1 May 3, 2012

Related U.S. Application Data

(63) Continuation-in-part of application No. 29/362,747, filed on May 28, 2010, now Pat. No. Des. 651,310.

(51) Int. Cl.
*A61B 17/56* (2006.01)
*A61F 2/46* (2006.01)
(Continued)

(52) U.S. Cl.
CPC .............. *A61F 2/461* (2013.01); *A61B 17/28* (2013.01); *A61B 17/282* (2013.01);
(Continued)

(58) Field of Classification Search
CPC ............... A61B 17/28; A61B 17/2804; A61B 17/2812; A61B 17/2816; A61B 17/282; A61B 17/2833; A61B 17/2841; A61B 17/29; A61B 17/2909; A61B 17/8894; A61B 2017/2837; A61B 2017/2845; A61B 2017/2908; A61B 2017/291; A61B 2017/2919; A61B 2017/2924; A61B 2017/2926; A61B 2017/2927; A61B 2017/2931; A61B 2017/2932; A61B 2017/2938; A61B 2017/2939; A61B 2017/294; A61F 2/46; A61F 2/4601; A61F 2/4603; A61F 2/4605; A61F 2/4606; A61F 2/4607; A61F 2/4609; A61F 2/461; A61F 2/4611; A61F 2/4612; A61F 2/4614; A61F 2/4684; A61F 2002/4615; A61F 2002/4622; A61F 2002/4623; A61F 2002/4624; A61F 2002/4625; A61F 2002/4627; A61F 2002/4628; B25B 1/04; B25B 1/2426; B25B 1/2431; B25B 5/04; B25B 5/16; B25B 5/163; B25B 7/00; B25B 7/02; B25B 7/04; B25B 7/14; B25B 7/16; Y10T 29/539; Y10T 29/53909; Y10T 29/53943
USPC ...... 606/86 R, 87, 88, 99, 86 A, 86 B, 90, 91, 606/100, 205–208; 81/300, 421, 422, 423; 623/22.12; 16/231, 232, 380, 386; 24/573.09; 29/268, 270, 278; 269/3, 6, 269/95, 254 CS; 403/150–151, 153, 154, 403/157, 316; 411/351, 315, 513
See application file for complete search history.

(56) References Cited

U.S. PATENT DOCUMENTS 4,083,642 A * 4/1978 Journee ..................... 403/316
4,601,289 A 7/1986 Chiarizzio et al.
(Continued)

*Primary Examiner* — Kevin T Truong
*Assistant Examiner* — Tracy Kamikawa
(74) *Attorney, Agent, or Firm* — Schwegman Lundberg & Woessner, P.A.

(57) ABSTRACT

An orthopedic implant inserter is provided with removable jaws. The jaws are connected to handles of the inserter by retainers. Each retainer includes a shaft and a latch. The shaft is configured to be received within mounting bores of a jaw and the associated handle. The latch is connected to the shaft and movable between a release configuration and a retaining configuration. In the release configuration, the shaft is removable from the mounting bores and the jaw is thereby removable from the associated handle. In the retaining configuration, the shaft is secured within the mounting bores and the jaw is thereby secured to the associated handle.

23 Claims, 8 Drawing Sheets

(51) Int. Cl.
*A61B 17/29* (2006.01)
*A61B 17/28* (2006.01)
*A61F 2/38* (2006.01)
*A61F 2/30* (2006.01)

(52) U.S. Cl.
CPC .... *A61B 17/2804* (2013.01); *A61B 2017/2845* (2013.01); *A61B 2017/2927* (2013.01); *A61F 2/3859* (2013.01); *A61F 2002/30471* (2013.01); *A61F 2002/30507* (2013.01); *A61F 2002/30563* (2013.01); *A61F 2002/30565* (2013.01); *A61F 2002/4622* (2013.01); *A61F 2002/4628* (2013.01); *A61F 2002/4681* (2013.01)

(56) References Cited

U.S. PATENT DOCUMENTS

| | | |
|---|---|---|
| 5,059,196 A | 10/1991 | Coates |
| 5,324,293 A | 6/1994 | Rehmann |
| 5,417,693 A | 5/1995 | Sowden et al. |
| 5,423,826 A * | 6/1995 | Coates ............... A61B 17/1728 606/281 |
| 5,486,181 A | 1/1996 | Cohen et al. |
| 5,540,697 A | 7/1996 | Rehmann et al. |
| 5,683,464 A | 11/1997 | Wagner et al. |
| 5,732,992 A | 3/1998 | Mauldin |
| 6,261,296 B1 * | 7/2001 | Aebi et al. ........................ 606/90 |
| 6,540,785 B1 | 4/2003 | Gill et al. |
| 6,551,316 B1 * | 4/2003 | Rinner et al. ................... 606/57 |
| 6,579,296 B1 * | 6/2003 | Macey ........................ 606/86 R |
| 6,626,913 B1 | 9/2003 | McKinnon et al. |
| 6,719,794 B2 | 4/2004 | Gerber et al. |
| 6,743,258 B1 | 6/2004 | Keller |
| 6,918,324 B2 * | 7/2005 | Hsien ........................... 81/427.5 |
| 6,974,480 B2 | 12/2005 | Messerli et al. |
| 7,037,311 B2 | 5/2006 | Parkinson et al. |
| 7,048,742 B2 | 5/2006 | Keller |
| 7,060,073 B2 | 6/2006 | Frey et al. |
| 7,150,761 B2 | 12/2006 | Justin et al. |
| 7,156,004 B1 * | 1/2007 | Whitehead et al. ............. 81/420 |
| 7,338,497 B2 | 3/2008 | Coon et al. |
| 7,776,044 B2 | 8/2010 | Pendleton et al. |
| 2003/0109929 A1 | 6/2003 | Keller |
| 2004/0215200 A1 | 10/2004 | Tornier et al. |
| 2005/0139422 A1 * | 6/2005 | Riley ............................... 182/82 |
| 2005/0288788 A1 | 12/2005 | Dougherty-Shah |
| 2006/0142777 A1 * | 6/2006 | Bastian ............................ 606/88 |
| 2009/0036909 A1 | 2/2009 | Perry et al. |

* cited by examiner

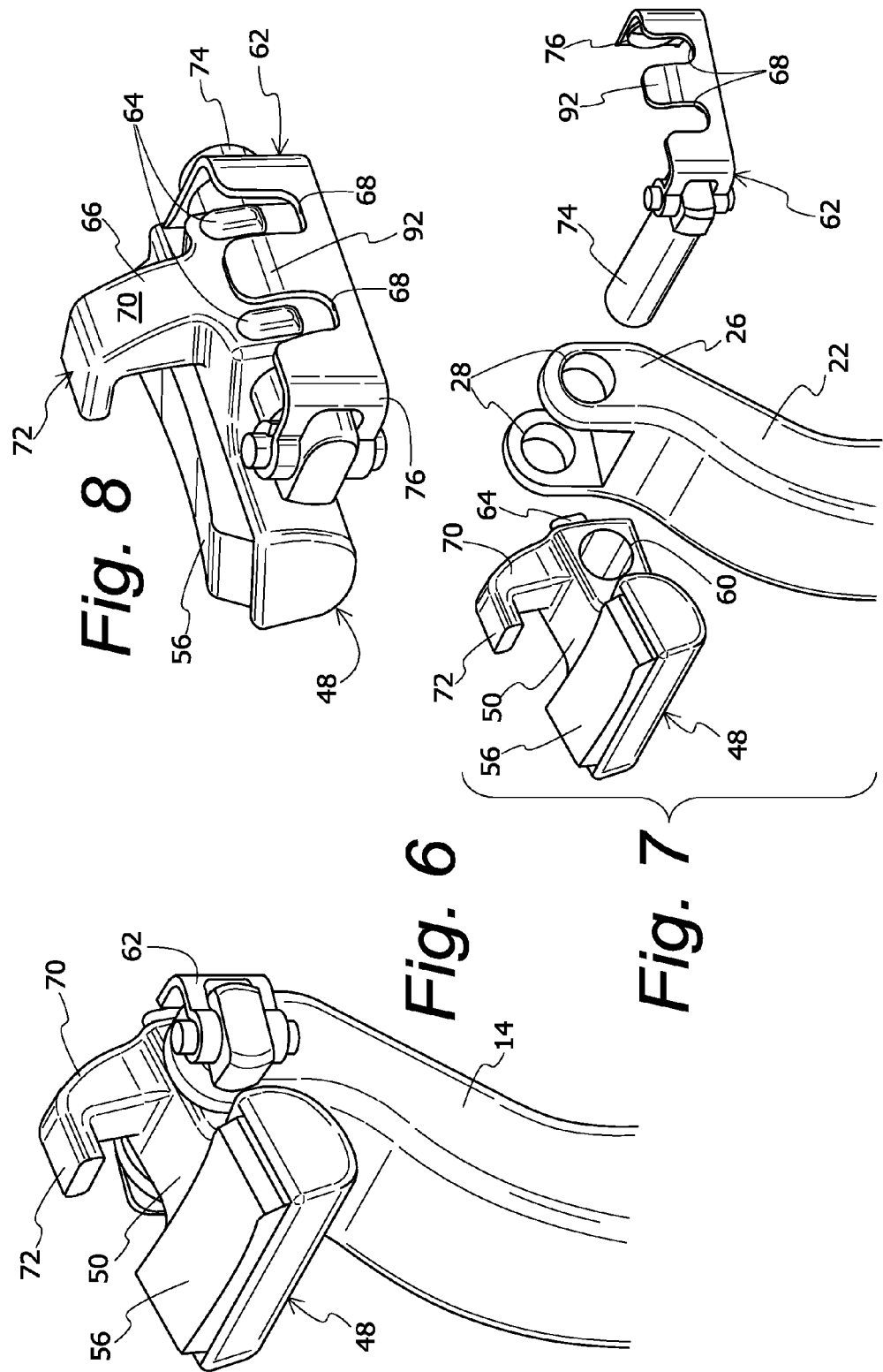

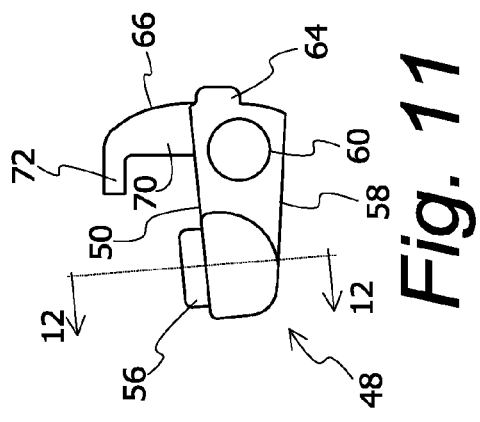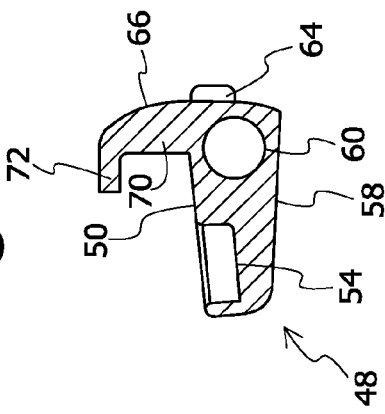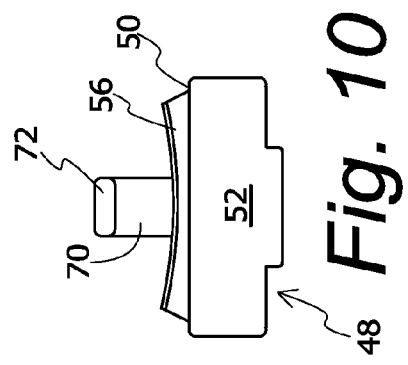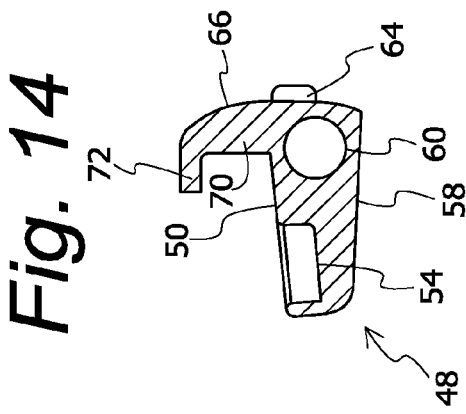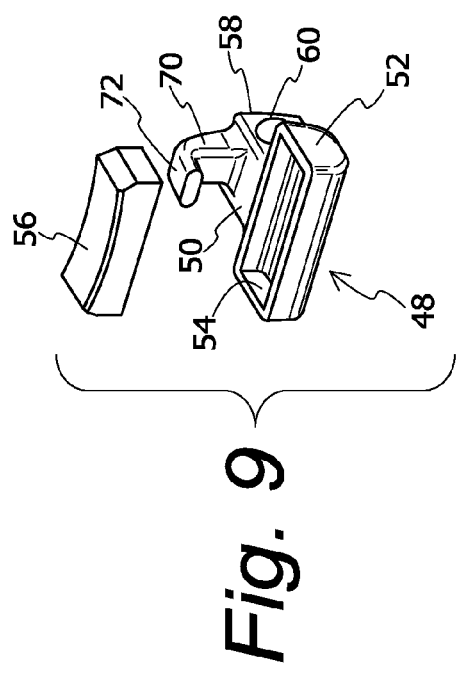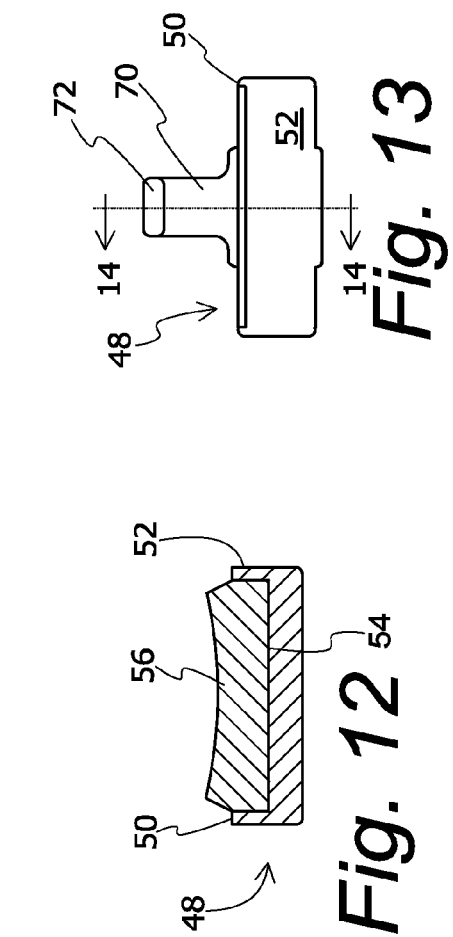

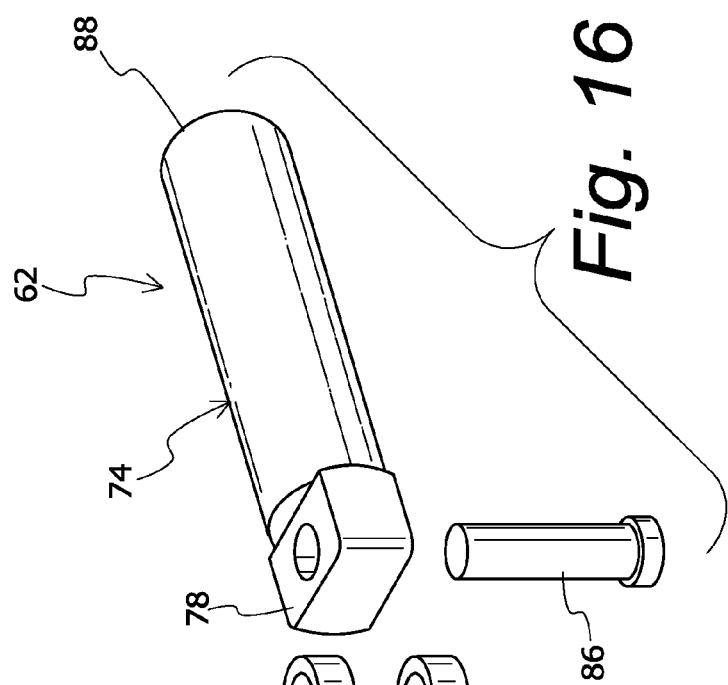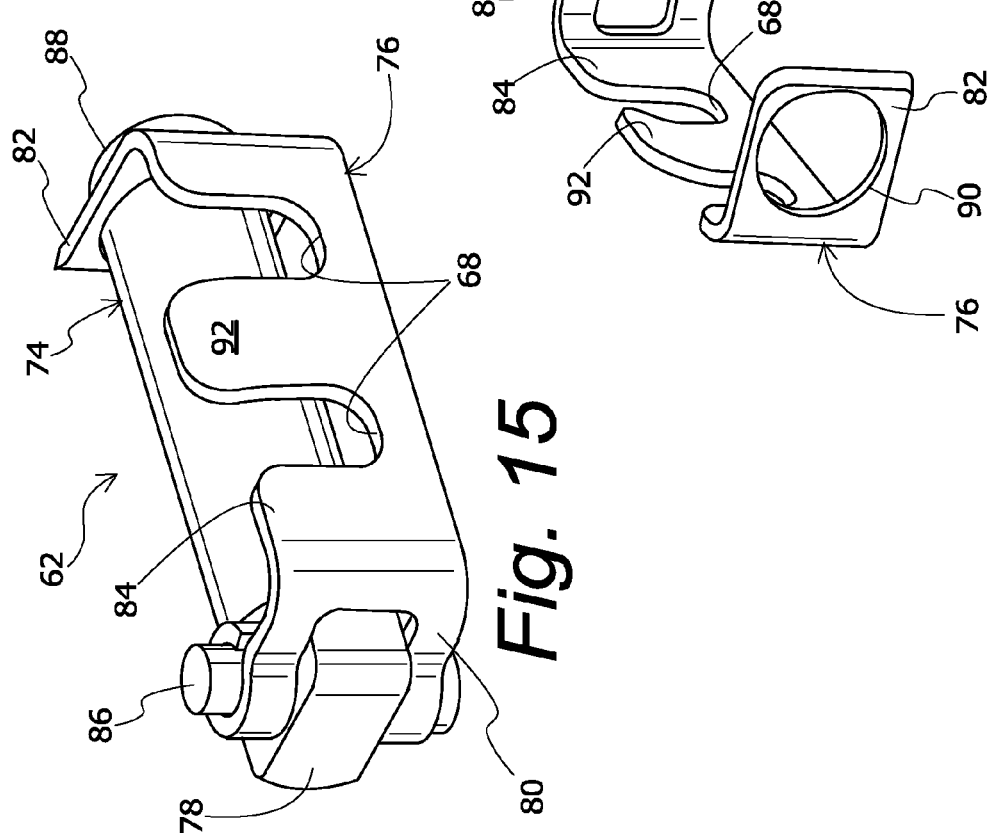

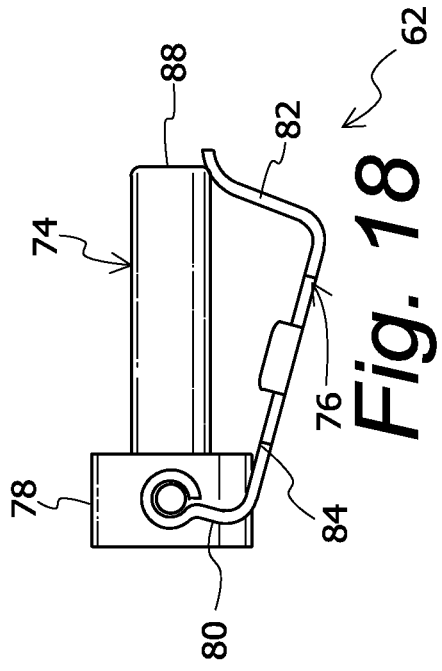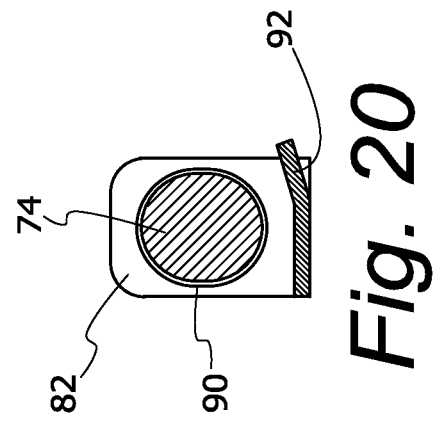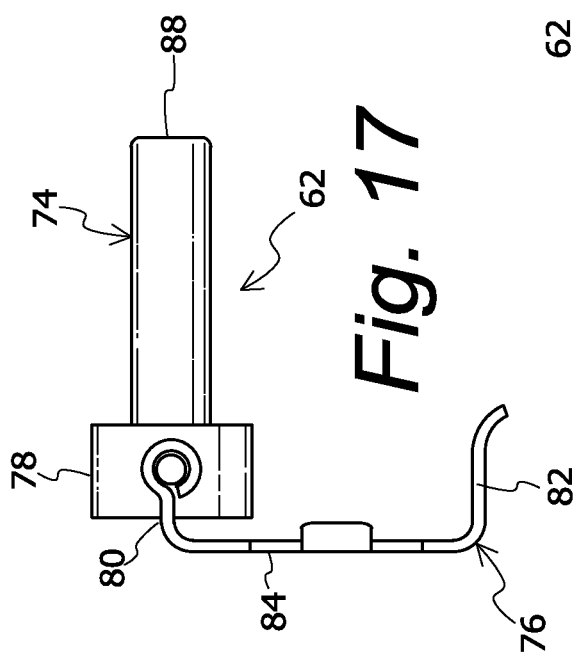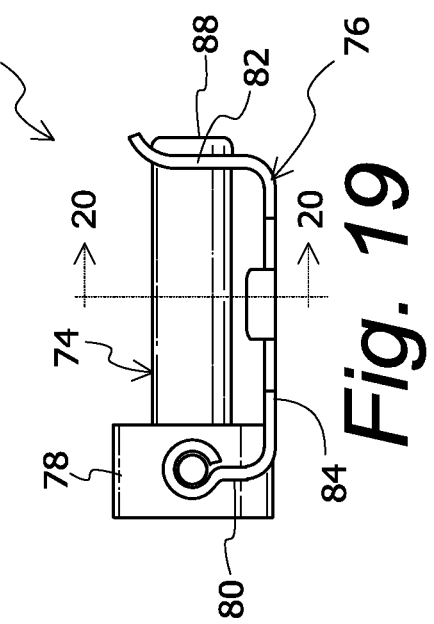

ORTHOPEDIC IMPLANT INSERTER WITH REMOVABLE JAWS

CROSS-REFERENCE TO RELATED APPLICATIONS

This application claims the benefit under Title 35, U.S.C. §120 of U.S. Design patent application Ser. No. 29/362,747, filed on May 28, 2010 and entitled PROSTHESIS IMPACTION AND EXTRACTION TOOL.

BACKGROUND

1. Field of the Disclosure

The present subject matter relates to systems and methods for delivering a device to a selected location within the body. More particularly, the present subject matter relates to an inserter for deploying an orthopedic component or implant within the body and methods of using the same.

2. Background

Various devices are known for inserting, positioning, and/or impacting orthopedic implants or "provisionals" (i.e., temporary implant simulators for ascertaining the proper size and shape for a permanent implant) in orthopedic procedures. These devices will be collectively and interchangeably referred to herein as "orthopedic implant inserters" or "implant inserters" or "inserters," for short, and though illustrated in the context of insertion of a femoral component in an orthopedic knee procedure, such inserters may be used with other body implants (e.g., implants in the tibial baseplate region) and the present disclosure is not limited to inserters used only with femoral implants. Also, as used herein, "implants" includes actual implants, implant components, and provisionals.

Implant inserters have been commercially available in a variety of shapes and configurations. Typically, such implant inserters have been relatively large, with associated weight and ergonomic shortcomings. Further, orthopedic procedures often involve physically impacting or hammering the inserter with a mallet to install the implant. Over time, this usage can damage the inserter itself and result in undesirable wear and tear to that portion of the inserter to which the implant is temporarily mounted during implantation. To prevent damaging the implant, the entire inserter is periodically replaced with a costly new one.

Thus, there continues to be a need for implant inserters that advance the state of the art of implant inserter design and that may address one or more shortcomings of prior devices including, but not limited to, those mentioned above.

SUMMARY

In accordance with one aspect of the present disclosure, an orthopedic implant inserter comprises first and second facing handles joined for relative movement toward and away from one another. A first implant-engaging member is mounted on the first handle and a second implant-engaging member is mounted on the second handle. At least one of the implant-engaging members is removably mounted on the associated handle.

In accordance with another aspect of the present disclosure, an orthopedic implant inserter comprises first and second facing handles joined for relative movement toward and away from one another. A first implant-engaging jaw is removably mounted to the first handle and a second implant-engaging jaw is removably mounted to the second handle. Each implant-engaging jaw is pivotal with respect to the associated handle and removably secured thereto by a retainer. Each retainer is movable between a retaining configuration in which the implant-engaging jaw is secured to the associated handle and a release configuration in which the implant-engaging jaw is removable from the associated handle. Each retainer engages and biases the associated implant-engaging jaw to a selected pivotal position when in the retaining configuration.

In accordance with yet another aspect of the present disclosure, an orthopedic implant inserter jaw is provided for removable mounting on the handle of an orthopedic implant inserter configured to receive a retainer that includes a shaft and a latch cooperatively associated with the shaft and which retainer is movable between a retaining configuration in which the retainer is secured to the handle and a release configuration in which the retainer is removable from the handle. The jaw comprises a base, a through bore in the base for removably receiving a shaft of a retainer, and an implant support and impact surface on the base. The jaw further includes an implant-engaging surface carried on the base for engaging an implant in a desired position with respect to the base and an orientation structure on the base that cooperates with a retainer latch for orienting the jaw in one position on the handle.

As made clearer below, there are several aspects of the present subject matter which may be embodied separately or together in the methods and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

BRIEF DESCRIPTION OF THE DRAWINGS

FIG. 6 is a perspective detail view of a handle, jaw, and retainer of the inserter of FIG. 2, with the retainer in a retaining configuration;

FIG. 7 is an exploded view of the handle, jaw, and retainer of FIG. 6, with the retainer in a release configuration;

FIG. 8 is a perspective view of the jaw and retainer of FIG. 6 taken from a different viewpoint than FIG. 6, with the handle omitted for illustrative purposes;

FIG. 9 is an exploded perspective view of the jaw and an implant support and impact surface of FIG. 6;

FIG. 10 is a front elevational view of the jaw and support surface of FIG. 6;

FIG. 11 is a side elevational view of the assembled jaw and support surface of FIG. 10;

FIG. 12 is a cross-sectional view of the jaw and support surface of FIG. 11, taken through the line 12-12 of FIG. 11;

FIG. 13 is a front elevational view of the jaw of FIG. 6, with the support surface omitted;

FIG. 14 is a cross-sectional view of the jaw of FIG. 12, taken through the line 14-14 of FIG. 13;

FIG. 15 is a perspective view of a retainer of FIG. 2 in a retaining configuration;

FIG. 16 is an exploded view of the retainer of FIG. 15;

FIG. 17 is a top plan view of the retainer of FIG. 15 in a release configuration;

FIG. 18 is a top plan view of the retainer of FIG. 15 in an intermediate configuration;

FIG. 19 is a top plan view of the retainer of FIG. 15 in a retaining configuration; and FIG. 20 is a cross-sectional view of the retainer of FIG. 19, taken through the line 20-20 of FIG. 19.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
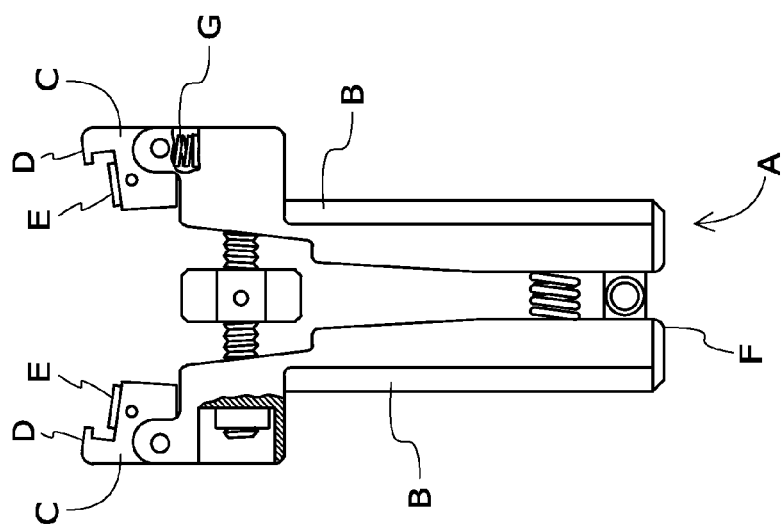
FIG. 1 is a front elevational view of an orthopedic implant inserter according to a prior art design.

By way of background, a prior art inserter "A" is illustrated in FIG. 1 and includes a pair of clamping handles "B" with a space therebetween to receive a portion of an implant. Each handle B includes at its outer or distal end an implant-engaging member or jaw "C" which is pivotally connected to the handle B. Each jaw C has a small implant-engaging surface "D," with the surfaces D of the jaws C facing each other. The handles B are movable toward and away from each other to alternatively engage and disengage from an implant positioned therebetween. The surfaces D are configured to be received within side slots or recesses of the implant when the jaws C are in contact with the implant. Each jaw C is biased to an inwardly pivoted position by a compression spring "G" (only one of which is visible in FIG. 1). The compression springs G are relatively large, thereby contributing to the increased size of the inserter A. In addition to the surfaces D, each jaw C further includes an implant support and impact surface or pad "E" which engages an underside of the implant to apply insertion force against the implant during positioning or implantation, as will be described in greater detail herein.

In use, the implant is secured in place between the jaws C, in contact with the surfaces D and the pads E. The inserter A is then oriented and advanced to position the implant at a selected location within the body (e.g., at or adjacent to a prepared portion of a femur). With the implant in place, the proximal end "F" of the inserter A is impacted (e.g., using a mallet) to fully seat the implant into the target site. The impact pads E are the primary means by which force is applied from the inserter A to the implant. The impact pads E contact the implant over a large surface area, so it will be appreciated that they spread the force and reduce the impact stress experienced by the implant. The surfaces D (which are primarily intended to secure the implant in place or orient it during delivery to the selected location) substantially do not function to transmit impact forces to the implant. By distributing the impact stress over a greater area of surfaces, the risk of damaging the surfaces D and/or the implant itself is reduced.

One disadvantage of the foregoing design is that the jaws C, while pivotal, are fixedly secured to the handles B. Thus, if the impact pad E or another portion of the jaw C becomes damaged or worn after repeated use, the entire inserter A becomes unusable.

Turning now to the present invention and to a device that illustrates various aspects thereof, FIGS. 2-5 show an exemplary orthopedic implant inserter 10 according to the present disclosure. As pointed out earlier, unless explicitly indicated otherwise, the subject matter of this description is not limited to any particular orthopedic implant inserter or to an actual implant or a provisional implant. The inserter 10 includes a first handle 12 and a second handle 14 which are joined for relative movement toward and away from one another. In the illustrated embodiment, the handles 12 and 14 are pivotally connected to each other at or adjacent to their bottom end 16 by a pivot pin 18. The inserter 10 may further include a biasing component which biases the handles 12 and 14 away from each other, such as a spring of any suitable form and illustrated as a compression spring 24. The illustrated handles 12 and 14 are substantially similar to each other, with each having a generally linear grip portion 20 and an arm 22 extending from an upper or distal end of the grip portion 20. The grip portions 20 are intended to be gripped by hand during use of the inserter 10 (with one hand grasped around both grip portions 20), so it may be advantageous for the grip portions 20 to be ergonomically designed, with a rounded outside-facing gripping surface and curved hand rests at each end, allowing it to be more comfortably gripped. Other configurations may also be employed, so it should be understood that the illustrated embodiment is merely exemplary.

Figure 3:
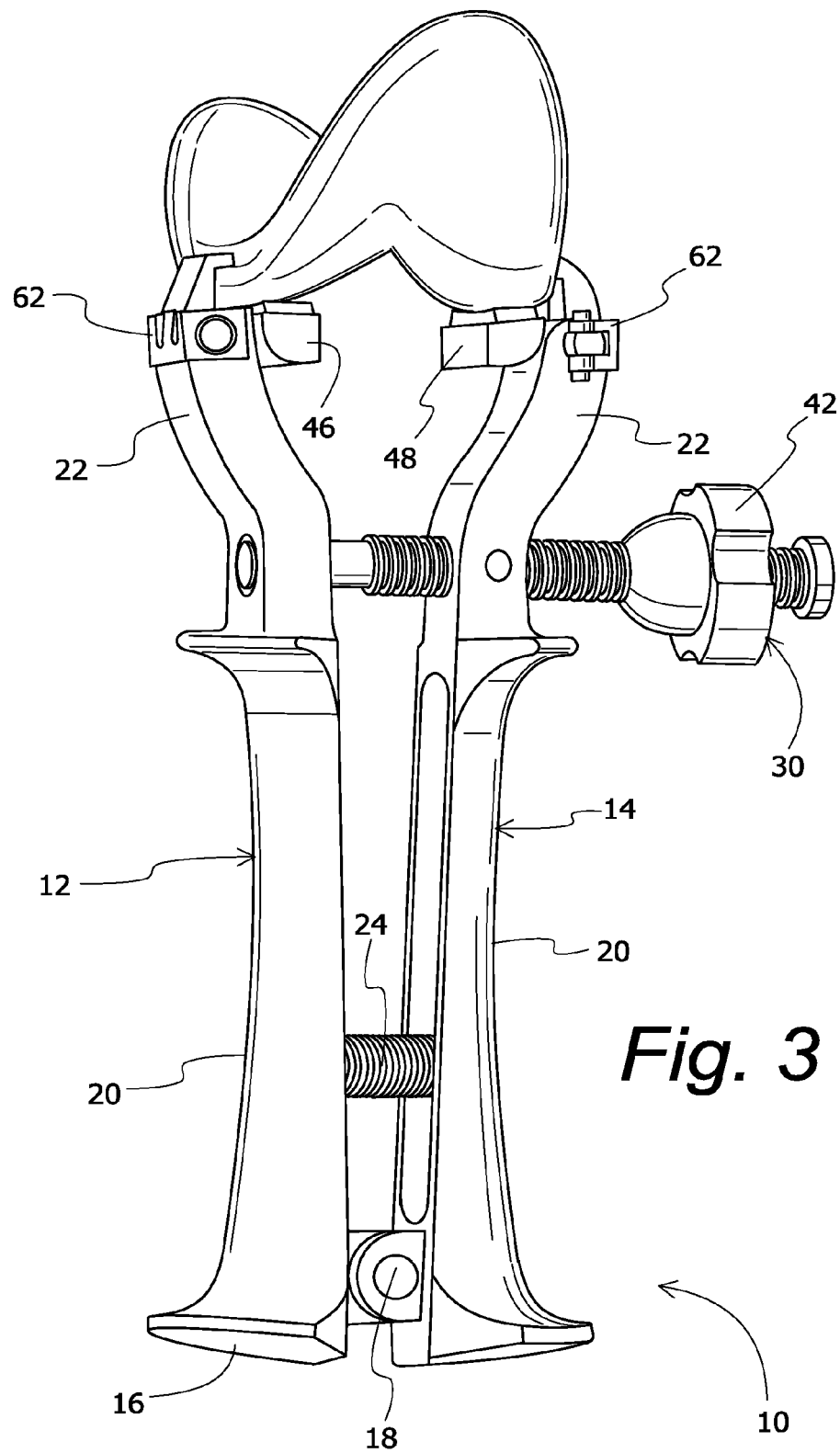
FIG. 3 is a perspective view of the inserter of FIG. 2 engaged with an implant.
Figure 4:
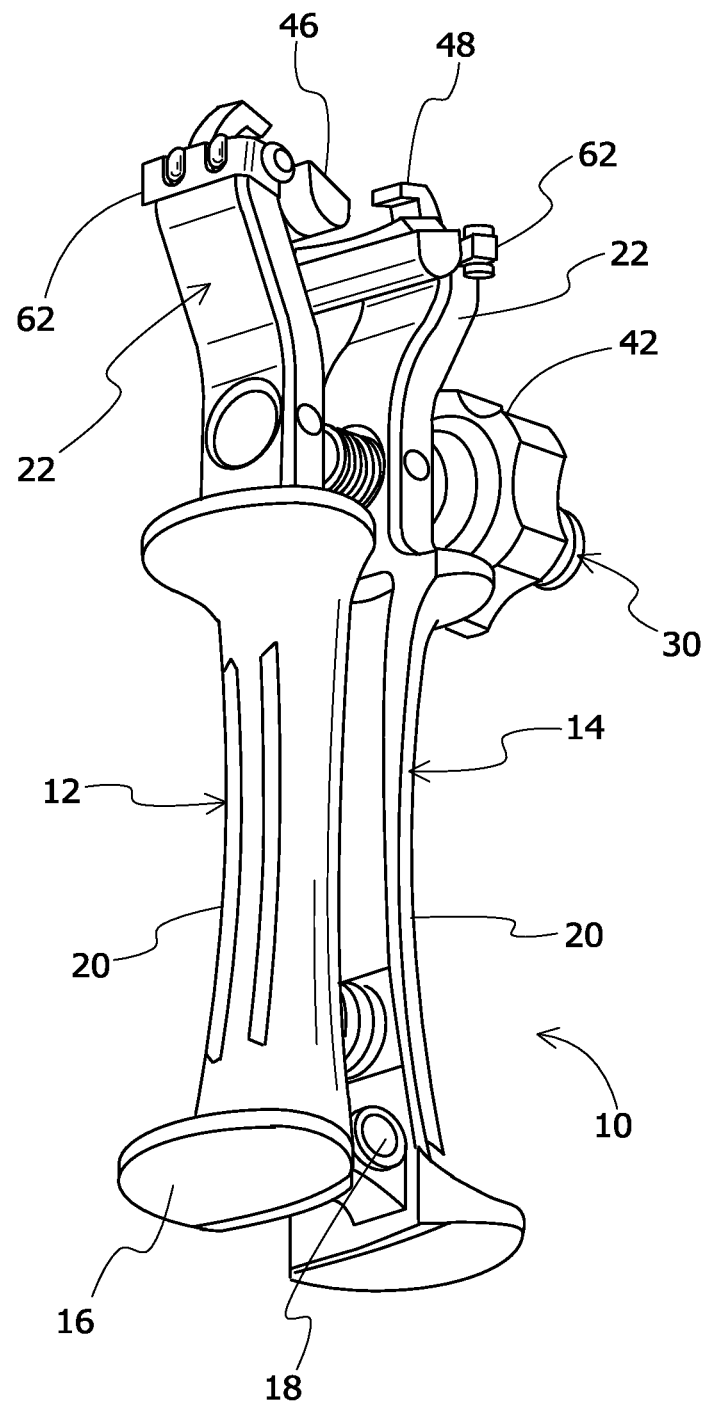
FIG. 4 is a perspective view of the inserter of FIG. 2.

The illustrated arms 22 are integrally formed with the associated grip portion 20, which may be advantageous to provide relatively strong and durable handles 12 and 14. The exact shape of the arms 22 depends on the nature of the implant to be handled by the inserter 10, with FIG. 3 showing an implant suitable for use with the illustrated arcuate arms 22. As inserters according to the present disclosure may be used in combination with a wide variety of differently shaped implants, the illustrated arcuate arms 22 should be considered exemplary, rather than limiting or exclusive. Each illustrated arm 22 has a forked upper end 26 (FIG. 5) with a pair of aligned arm mounting bores 28. The arm bores 28 provide a mounting bearing for mounting an implant engaging member of jaw 46, 48, as will be described in greater detail below.

The handles 12 and 14 may be made of any suitably rigid and durable material such as metal or a rigid polymer. Most preferably, the handles 12 and 14 are made of a medical-grade metal, such as surgical stainless steel. Other materials and material constructions, such as composites and laminates, may also be used without departing from the scope of the present disclosure.

Figure 2:
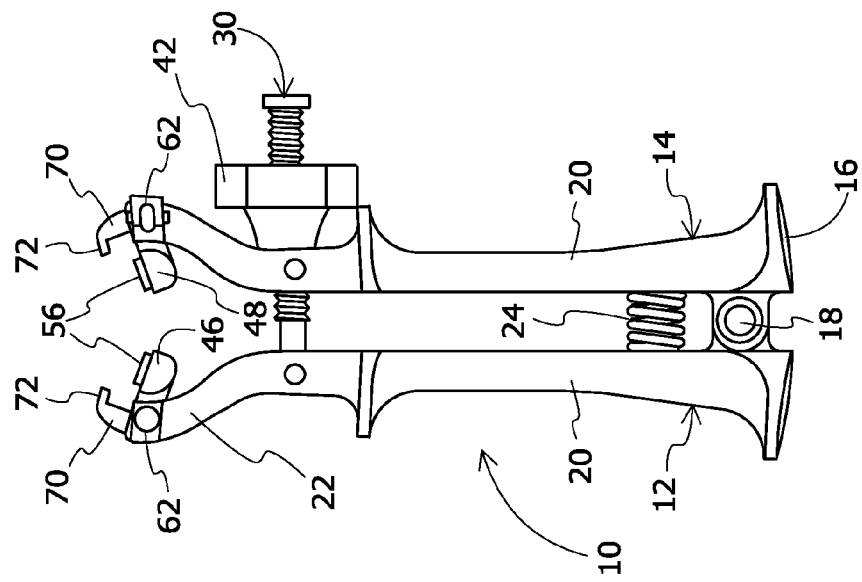
FIG. 2 is a front elevational view of an orthopedic implant inserter according to an aspect of the present disclosure.

The inserter 10 may further include an adjuster 30 for selectively adjusting the separation between the handles 12 and 14. The adjuster is one way to allow the handles 12 and 14 to be moved away from each other to accommodate an implant therebetween and then moved toward each other to engage the implant. The illustrated embodiment of the adjuster 30 connects the handles 12 and 14 to each other and provides for translation of the handles toward and away from one another. In the illustrated embodiment, a cylindrical shaft 32 of the adjuster 30 passes through a hole or opening 34, 36 in each of the handles 12 and 14. In the embodiment of FIG. 2, the hole 34 of the first handle 12 receives an end portion 38 of the shaft 32 which is held in place by a pin 44. In contrast, the hole 36 of the second handle 14 is threaded and receives a threaded portion 40 of the shaft 32. When the adjuster 30 is rotated about the central longitudinal axis of the shaft 32, the second handle 14 is advanced along the length of the shaft 32, either toward or away from the first handle 12, depending on the direction in which the adjuster 30 is rotated. The threads of the shaft 32 may interact with the threads of the hole 36 in the second handle 14 to provide a ratcheting effect that prevents the handles 12 and 14 from being forcibly moved toward or away from each other without rotating the adjuster 30. If provided, the adjuster 30 may further include a knob or dial 42 or the like which can by comfortably grasped by a user to rotate the adjuster 30.

It will be appreciated that, by reason of the pivotal attachment of the arms by the pivot pin 18 at the bottom end 16 of the handles 12 and 14, operating the adjuster 30 will cause the upper ends 26 of the handles 12 and 14 to pivot toward and away from each other. As noted previously, the configuration of FIGS. 2-5 is only one way of connecting the handles 12 and 14 and advancing them toward and away from each other, and other means of movably connecting the handles 12 and 14 and advancing them toward and away from each other may also be employed without departing from the scope of the present disclosure.

To cooperate with an orthopedic implant, the inserter 10 further includes a first implant-engaging member or jaw 46 connected to the arm 22 of the first handle 12 and second implant-engaging member or jaw 48 connected to the arm 22 of the second handle 14. The upper end portion 26 of the second handle 14 and the second jaw 48 are illustrated in greater detail in FIGS. 6-8, although it should be understood that the upper end 26 of the first handle 12 and the first jaw 46 are substantially identical thereto, so the discussion which follows applies equally to both jaws 46 and 48.

Each jaw 48 (shown in greater detail in FIGS. 9-14) includes a base 50 which is configured to support the other components of the jaw 48. In the illustrated embodiment, the base 50 has a generally T-shaped profile (when viewed from above), although other profiles may also be employed without departing from the scope of the present disclosure.

The illustrated base 50 has a support portion 52 which defines a cavity 54 (FIGS. 9, 12, and 14) for receiving an implant support and impact surface or cushion or pad 56. The pad 56 may be thicker than the cavity 54 is deep, allowing a top portion of the pad 56 to extend above a top surface of the base 50. Alternatively, the support portion 52 of the base 50 may omit the cavity 54 (having instead, for example, a relatively planar or even raised top surface) and serve as a platform or substrate to which the pad 56 is secured or integrally formed. The function of the pad 56 is to contact the implant to provide a cushioning effect upon application of an impact force to the inserter 10 (as will be described in greater detail below). Accordingly, it is advantageous for the pad 56 to extend above the top surface of the base 50 and to be more pliable than the rest of the jaw 48. Thus, the jaw 48 may be comprised of a relatively durable and rigid material, such as stainless steel, while the pad 56 is comprised of a more elastic or flexible material, such as rubber or another elastomeric material, or a polymeric material.

The jaw 48 also includes a projection 70 which extends generally upwardly from a hinge portion 58 thereof. The projection 70 includes an inwardly facing post or flange or other implant-engaging surface 72, which is configured to engage the implant, such as by receipt within a slot or opening of the implant, as in FIG. 3. The exact shape of the projection 70 and implant-engaging surface 72 depends on the nature of the implant, so it will be appreciated that, for differently shaped implants, differently shaped projections and implant-engaging surfaces may be preferable. Therefore, the illustrated projection 70 and implant-engaging surface 72 are intended to be exemplary instead of limiting.

At least one of the jaws 46, 48, but more advantageously both of the jaws 46 and 48, are removably mounted on the associated handle 12, 14, which allows the jaw to be removed and replaced if it has become damaged or worn or if it becomes desirable to install a differently shaped jaw. In an exemplary embodiment, this is accomplished by the use of retainers 62 (FIGS. 15-20) which removably mount the jaws 46 and 48 on the associated handles 12 and 14.

To accommodate the retainers 62 (which will be described in greater detail herein), the hinge portion 58 of the jaw base 50 includes a through bore 60 (FIGS. 7 and 11), which cooperates with the arm bores 28 to define a bearing. The hinge portion 58 of the base 50 is sized and configured to be positioned in the forked upper end 26 of the associated handle arm 22, with the jaw bore 60 substantially aligned with the arm bores 28. In an exemplary embodiment, the hinge portion 58 has a width generally the same as the width of the gap between the forks of the associated arm 22. If so dimensioned, when the jaw 48 is mounted in place, the hinge portion 58 will fit snugly (without binding) within the forked upper end 26, substantially preventing lateral movement or "wiggling" of the jaw 48 between the forks of the handle 14.

The retainer 62 is illustrated in FIGS. 15-20 and is comprised of a pin or shaft 74 and a latch 76 cooperatively associated with the shaft 74. The shaft 74 is received within the bearing defined by alignment of the arm bores 28 and the jaw bore 60 when the hinge portion 58 of the jaw 48 is located within the forked upper end 26 of the associated arm 22. The shaft 74 so positioned serves as a hinge or pivot pin, the axis of which the jaw 48 can be pivoted about with respect to the associated handle 14.

Figure 5:
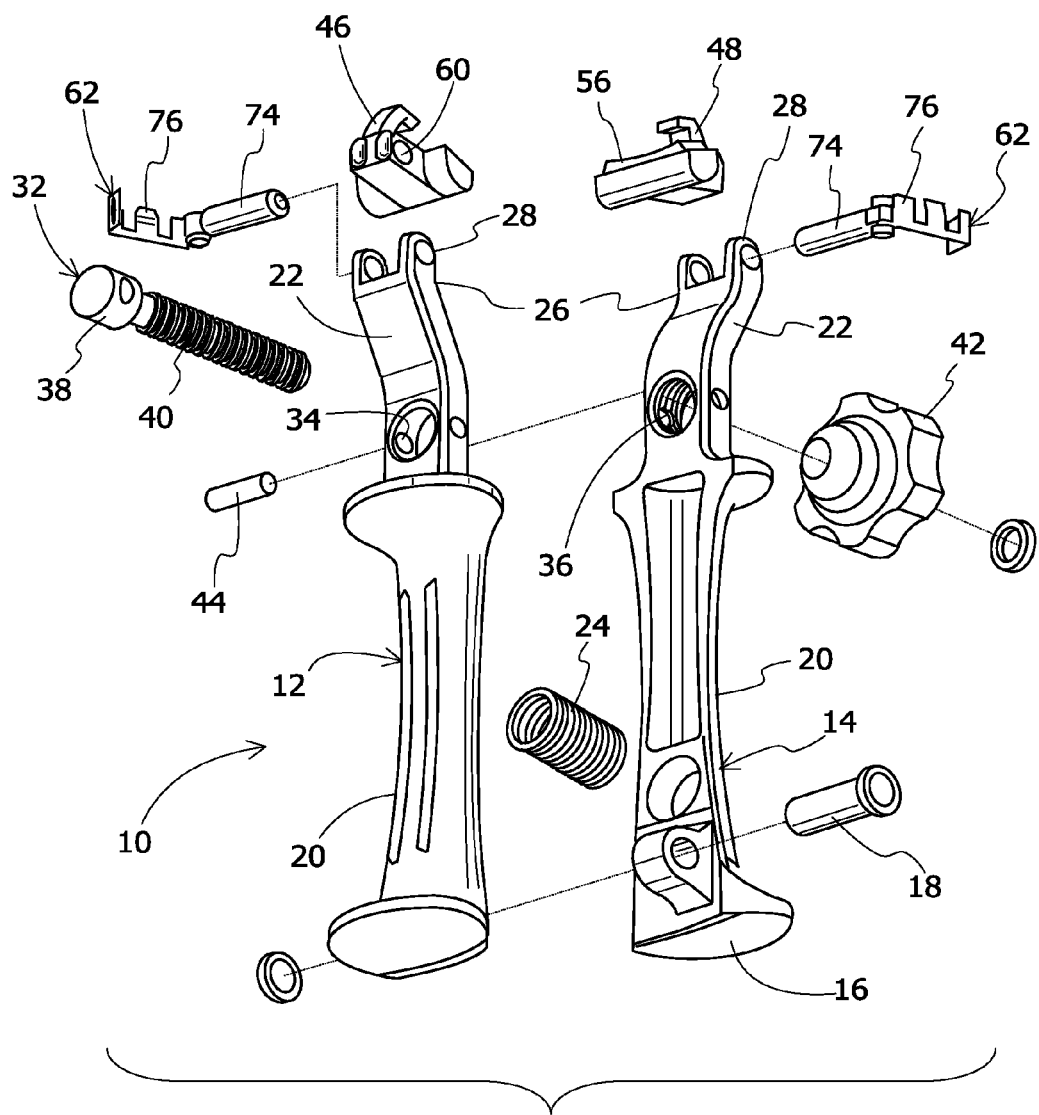
FIG. 5 is an exploded view of the inserter of FIG. 2.

The latch 76 is cooperatively associated with the shaft 74 so as to be movable between a retaining configuration in which the shaft 74 is retained in the aligned mounting bores 28 and 60 (FIGS. 6 and 15) and a release configuration in which the shaft 74 is removable from the aligned mounting bores 28 and 60 (FIGS. 5 and 7). The latch 76 may be connected to the shaft 74 by any of a number of means, provided that it can move between the retaining and release configurations. In the illustrated embodiment, the latch 76 is pivotally connected to an end of the shaft 74. FIGS. 17-19 show the latch 76 being pivoted from the release configuration (FIG. 17) to an intermediate configuration (FIG. 18) to the retaining configuration (FIG. 19). Considered in the reverse order, FIG. 17-19 show the latch 76 being moved from the retaining configuration (FIG. 19) to the intermediate configuration (FIG. 18) to the release configuration (FIG. 17). Other means for connecting the latch 76 to the shaft 74 so as to be movable between the release and retaining configurations may also be employed without departing from the scope of the present disclosure.

The jaws 46 and 48 of the inserter 10 are attached to the respective handles 12 and 14 as follows. First, the hinge portion 58 of the base 50 is positioned in the forked upper end 26 of the associated handle 12,14, with the jaw bore 60 substantially aligned with the arm bores 28 to define a bearing for the shaft 74, with the support portion 52 pointed toward the opposing handle 14, 12, and the pad 56 oriented upwardly (i.e., away from the inserter 10). With the respective jaw 46, 48 properly positioned, the shaft 74 of a retainer 62 is inserted through the aligned mounting bores 28 and 60, being mindful of the orientation of the orientation surfaces 64 and 68. When the shaft 74 is fully or at least adequately inserted through the bores 28 and 60, the latch 76 may be pivoted or otherwise moved to lock the retainer 62 in place. So attaching the latch 76 secures the jaw 46, 48 to the associated handle 12, 14, while also allowing the jaw 46, 48 to pivot with respect to the handle 12, 14, as described above.

To remove the jaw 46, 48 from the handle 12, 14, the latch 76 is pivoted or moved in the opposite direction to unlock the retainer 62. The shaft 74 can then be slid out of the bores 28 and 60, which disengages the jaw 46, 48 from the handle 12, 14.

The illustrated latch 76 is a generally C- or U-shaped component with generally parallel first and second legs 80 and 82 which are connected by a crossbeam or midsection 84. The first leg 80 is pivotally connected to one end 78 of the shaft 74 by a pin 86 (FIG. 16) or the like. The second leg 82 is configured to removably engage the opposite end 88 of the shaft 74 in the retaining configuration (FIG. 15). In the illustrated embodiment, the second leg 82 has an opening or aperture 90 (FIGS. 16 and 20) which is configured to receive and retain the opposite end 88 of the shaft 74 in the retaining configuration. To that end, the second leg 82 may be outwardly flared or angled or otherwise contoured (as best illustrated in FIGS. 17-19). As the latch 76 pivots to the retaining configuration, the second leg 82 will be forced into contact with the contoured opposite end 88 of the shaft 74 (FIG. 18) and flex or bend outwardly (i.e., away from the first leg 80) to clear the end 88 of the shaft 74. The resilience of the latch 76 seats the opposite end 88 of the shaft 74 within the opening 90 in the retaining configuration (FIG. 19). Accordingly, it may be advantageous for the latch 76 to be comprised of a rigid material which can undergo minor bending without permanent deformation. Suitable materials for the latch 76 include, but are not limited to, stainless steel.

As for the midsection 84 of the latch 76, it may be advantageous for it to have a width generally the same as the width of the forked upper end 26 of the associated handle 14. If so configured, when the retainer 62 is latched in place, the legs 80 and 82 will fit snugly around the forked upper end 26, thereby preventing significant lateral movement or "wiggling" of the retainer 62 on the handle 14.

The latch 76 may optionally include one or more features which enhance the functionality of the retainer 62. For example, in the illustrated embodiment, the latch 76 includes a biasing feature, and more specifically the midsection 84 of the latch 76 includes a biasing member or surface 92. The biasing surface 92 of the midsection 84 is configured to contact the outer surface 66 of the jaw 48 (FIG. 8) and bias the jaw 48 to an inwardly pivoted position (FIG. 2) when the retainer 62 is latched onto the jaw 48 and handle 14. Advantageously, the biasing surface 92 is sufficiently rigid to bias the jaw 48 inwardly, but also capable of flexing or bending outwardly to accommodate some degree of outward pivotal motion of the jaw 48 when the inserter 10 is clamped onto an implant. The biasing surface 92 may be variously configured to have such functionality. For example, in the illustrated embodiment, the biasing member 92 is integrally formed with the latch 76, forming a flat spring, and inclined approximately 15° from the plane of the midsection 84 (FIG. 20) in the same direction that the legs 80 and 82 extend. However, other configurations of a biasing surface may also be employed without departing from the scope of the present disclosure.

The retainer 62, and the latch 76 in particular, may also include an orientation feature to reduce the chance of mis-assembly or mis-orientation of the jaw 48 on its respective handle 14. As illustrated, the latch 76 includes orientation structures 68 which are configured to cooperate with orientation structures 64 of the associated jaw 48, such that the orientation structures 64 and 68 accommodate each other in only one orientation, thereby dictating the orientation of the retainer 62 when the latch 76 is moved to the retaining configuration.

More specifically, in the illustrated embodiment, the hinge portion 58 of the jaw base 50 includes two orientation structures 64 which are provided as raised surfaces or projections positioned at the outer or outside-facing surface 66 of the jaw 48 (FIG. 8). The nature and shape of the orientation structures 64 may vary, depending on the shape of the structure(s) to which they are mated. For example, in the illustrated embodiment, the orientation structures 64 are provided as raised surfaces whereas, in other embodiments, the hinge portion 58 of the jaw 48 may be provided with depressions or cavities serving as orientation features. Further, there may be more or less than two orientation structures, depending on the shape and nature of the structure(s) to which the orientation structures are mated.

The illustrated orientation structures 64 are provided as a pair of vertically oriented, generally oval-, rectangle-, or "racetrack"-shaped projections. The projections 64 are shown as being identical to each other, but other embodiments may include orientation structures which are differently shaped from each other. The projections 64 may be relatively small and/or thin, as they merely provide an orienting function, rather than serving as force-bearing structures.

As for the orientation surfaces 68 of the latch 76, they are illustrated as generally U-shaped slots or receiving regions which at least partially receive the projections 64 of the jaw 48 when the retainer 62 is latched onto the jaw 48 and handle 14 (FIG. 8). FIG. 8 also shows how the biasing surface 92 contacts the outer surface 66 of the jaw 48 between the orientation surfaces 64, thereby providing an additional keying or orienting function. It will be appreciated that, if the orientation surface(s) of the jaw 48 are differently configured than what is illustrated, then the orientation surface(s) of the retainer 62 will also be differently configured to cooperate with them. The jaws and retainers may include other features and arrangements without departing from the scope of the present disclosure.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims.

What is claimed is:

1. An orthopedic implant inserter comprising:
first and second facing handles joined for relative movement with respect to one another in a first plane, the first handle including a first opening extending through the first handle and the second handle including a second opening extending through the second handle;
a first implant-engaging jaw removably mounted to the first handle;
a second implant-engaging jaw removably mounted to the second handle, the first and second implant-engaging jaws are spaced apart from and independent of one another, and each implant-engaging jaw is removable from its associated handle independent of removal of the other implant-engaging jaw; and
an adjuster configured to move the first and second handles away from and toward each other, the adjuster comprising:
a shaft that passes through the second opening in the second handle and the first opening in the first handle, the second handle configured to advance along a length of the shaft toward or away from the first handle to move the first and second implant-engaging jaws toward or away from each other; and
a knob configured to control the advancement of the second handle either toward or away from the first handle, the knob movable on a portion of the shaft extending beyond an external side of the second handle, wherein
each implant-engaging jaw comprises a base, an implant support, and a retainer that is movable between a retaining configuration in which the implant-engaging jaw is secured to the associated handle and a release configuration in which the implant-engaging jaw is removable from the associated handle, and
each retainer includes:
a shaft for insertion into mounting bores on the base of each implant-engaging jaw and the associated handle, the shaft of the retainer extending through the base of the respective implant-engaging jaw in a generally parallel orientation to the implant support of the respective implant-engaging jaw, wherein the shaft of each retainer extends in a second plane perpendicular to the first plane when the retainer is in the retaining configuration; and
a latch comprising:
a first leg for pivotally connecting to a first end of the shaft of the retainer via a pin;
a second leg configured to removably engage a second end of the shaft of the retainer via an aperture;
a resilient cross beam connecting the first leg and the second leg; and
a biasing member extending from the resilient cross beam.

2. The orthopedic implant inserter of claim 1, further comprising an orienting arrangement defined by respective surfaces of each implant-engaging jaw base and the associated retainer which accommodates mounting of the implant-engaging jaw to the associated handle in one orientation.

3. The orthopedic implant inserter of claim 2, wherein the orienting arrangement comprises at least one raised surface on one of the implant-engaging jaw base and the associated retainer and a receiving region defined in the other of the implant-engaging jaw base and the associated retainer for receiving the raised surface.

4. The orthopedic implant inserter of claim 1, wherein each latch is movable between the retaining configuration in which the shaft of each retainer is retained in the mounting bores of the associated implant-engaging jaw and handle and the release configuration in which the shaft of each retainer is removable from the mounting bores of the associated implant-engaging jaw and handle.

5. The orthopedic implant inserter of claim 1, wherein the second opening in the second handle is threaded and interacts with a threaded portion of the shaft of the adjuster and the first opening in the first handle receives an end portion of the shaft of the adjuster.

6. The orthopedic implant inserter of claim 1, wherein the shaft of the adjuster extends in a direction generally perpendicular to the first and second handles.

7. The orthopedic implant inserter of claim 1, wherein the first implant-engaging jaw is pivotally mounted to the first handle and the second implant-engaging jaw is pivotally mounted to the second handle.

8. The orthopedic implant inserter of claim 1, wherein the first and second facing handles are each monolithic.

9. An orthopedic implant inserter comprising:
first and second facing handles joined for relative movement with respect to one another in a first plane;
a first implant-engaging member pivotally mounted on the first handle;
a second implant-engaging member pivotally mounted on the second handle, each implant-engaging member comprising:
a base extending along a first axis,
a mounting bore disposed at a first end portion of the base, the mounting bore extending through the base along a pivot axis perpendicular to the first axis,
an implant support disposed at a second end portion of the base, the implant support being elongated in a direction substantially perpendicular to the first axis,
a projection extending in a substantially perpendicular direction from the base at the first end portion of the base, and
an implant-engaging surface extending in a substantially perpendicular direction from the projection and separate from the implant support, the implant-engaging surface facing the base and stopping short of overhanging the implant support,
the first and second implant-engaging members being spaced apart from and independent of one another, each implant-engaging member being removable from its associated handle independent of removal of the other implant-engaging member, wherein the pivoting of the first and second implant-engaging members on the respective first and second handles changes a distance between the first and second implant-engaging members;
a first retainer for removably mounting the first implant-engaging member on the first handle;
a second retainer for removably mounting the second implant-engaging member on the second handle, each of the first and second retainers movable between a retaining configuration in which the implant-engaging member is secured to the associated handle and a release configuration in which the implant-engaging member is removable from the associated handle, and the first and second retainers extending in a second plane perpendicular to the first plane when the first and second retainers are in the retaining configuration, wherein each retainer includes a shaft for engaging the mounting bore in the respective base and an aligned mounting bore in the associated handle; and
an adjuster configured to move the first and second handles away from and toward each other, the adjuster comprising:
a shaft that passes through an opening in each of the first and second handles, the second handle configured to advance along a length of the shaft of the adjuster toward or away from the first handle; and
a knob configured to control the advancement of the second handle either toward or away from the first handle, the knob movable on a portion of the shaft of the adjuster extending beyond an external side of the second handle.

10. The orthopedic implant inserter of claim 9, wherein each of the implant-engaging members is biased toward a selected pivotal position.

11. The orthopedic implant inserter of claim 9, wherein each retainer includes a surface engaging the respective implant-engaging member when the retainer is in the retaining configuration to bias the respective implant-engaging member toward a selected pivotal position.

12. The orthopedic implant inserter of claim 9, further comprising an orienting arrangement that allows operative mounting of at least one of the implant-engaging members on the associated handle in one orientation.

13. The orthopedic implant inserter of claim 12, wherein the orienting arrangement is defined by respective surfaces of the at least one of the implant-engaging members and the associated retainer.

14. The orthopedic implant inserter of claim 13, wherein the orienting arrangement comprises at least one raised surface on one of the at least one of the implant-engaging members and the associated retainer and a receiving region defined in the other of the at least one of the implant-engaging members and the associated retainer for receiving the raised surface.

15. The orthopedic implant inserter of claim 9, wherein each retainer further comprises a latch that is pivotally attached to an end of the shaft of the retainer and removably engageable with another end of the shaft of the retainer in the retaining configuration.

16. The orthopedic implant inserter of claim 15, wherein each implant-engaging member is pivotal about the pivot axis of the aligned mounting bores and each latch includes an integral surface that engages and biases the respective implant-engaging member toward a selected pivotal position when the latch is in the retaining configuration.

17. The orthopedic implant inserter of claim 9, wherein the first and second handles either move away from or toward each other depending on a direction that the knob is rotated.

18. The orthopedic implant inserter of claim 9, wherein the opening in the second handle is threaded and interacts with a threaded portion of the shaft of the adjuster.

19. The orthopedic implant inserter of claim 9, wherein the opening in the first handle receives an end portion of the shaft of the adjuster.

20. The orthopedic implant inserter of claim 19, wherein the end portion of the shaft of the adjuster is held in place in the opening in the first handle using a pin extending through the opening of the first handle in a direction perpendicular to an orientation of the shaft of the adjuster.

21. The orthopedic implant inserter of claim 9, wherein the shaft of the adjuster extends in a direction generally perpendicular to the first and second handles.

22. The orthopedic implant inserter of claim 9, wherein the shaft of each retainer extends through the associated handle and implant-engaging member when the retainer is in the retaining configuration.

23. The orthopedic implant inserter of claim 9, wherein the pivoting of the first and second implant-engaging members on the respective first and second handles changes a distance between the first and second implant-engaging members in the first plane.

* * * * *